United States Patent [19]

Koyama et al.

[11] Patent Number: 5,227,171
[45] Date of Patent: Jul. 13, 1993

[54] PROCESS FOR PRODUCING FLAVORED PHARMACEUTICAL PREPARATION FOR ORAL ADMINISTRATION USING A COLD WATER SOLUTION OF POLYVINYL ACETAL DIMETHYLAMINOACETATE

[75] Inventors: Ikuo Koyama, Hasuda; Kimihide Shimano, Ageo; Eri Makabe, Hatogaya; Yasuo Ozawa, Ageo, all of Japan

[73] Assignee: Taisho Pharmaceutical Co., Ltd., Japan

[21] Appl. No.: 623,422
[22] PCT Filed: Apr. 17, 1990
[86] PCT No.: PCT/JP90/00496
  § 371 Date: Dec. 13, 1990
  § 102(e) Date: Dec. 13, 1990
[87] PCT Pub. No.: WO90/12566
  PCT Pub. Date: Nov. 1, 1990

[30] Foreign Application Priority Data

Apr. 18, 1989 [JP]  Japan .................................. 1-98283

[51] Int. Cl.⁵ .......................... A61K 9/28; A61K 9/22
[52] U.S. Cl. .................................. 424/497; 424/501; 424/489; 424/490
[58] Field of Search ................. 424/78, 78.35, 497

[56] References Cited

U.S. PATENT DOCUMENTS

| | | | |
|---|---|---|---|
| 4,016,254 | 4/1977 | Seager | 514/197 |
| 4,533,562 | 8/1985 | Ikegami et al. | 424/494 |
| 4,892,740 | 1/1990 | Takasima et al. | 424/482 |
| 5,002,775 | 3/1991 | Toya et al. | 424/467 |

Primary Examiner—Thurman K. Page
Assistant Examiner—Peter F. Kulkosky
Attorney, Agent, or Firm—Lorusso & Loud

[57] ABSTRACT

The present invention relates to a process for producing a flavored pharmaceutical preparation for oral administraiton and more particularly to a process for producing a flavored pharmaceutical preparation for oral administration, characterized by spraying, in a moistened and heated air, a suspension of a drug or drug-containing particles dispersed in a cold water solution of polyvinyl acetal diethylaminoacetate, and drying the resulting fine particles. Therefore, the present invention has made it possible to provide a process for producing, at a high yield, a flavored pharmaceutical preparation for oral administration wherein the taste of a drug contained therein is well masked and whose bioavailability is as good as that of a powder of the drug itself.

14 Claims, 1 Drawing Sheet

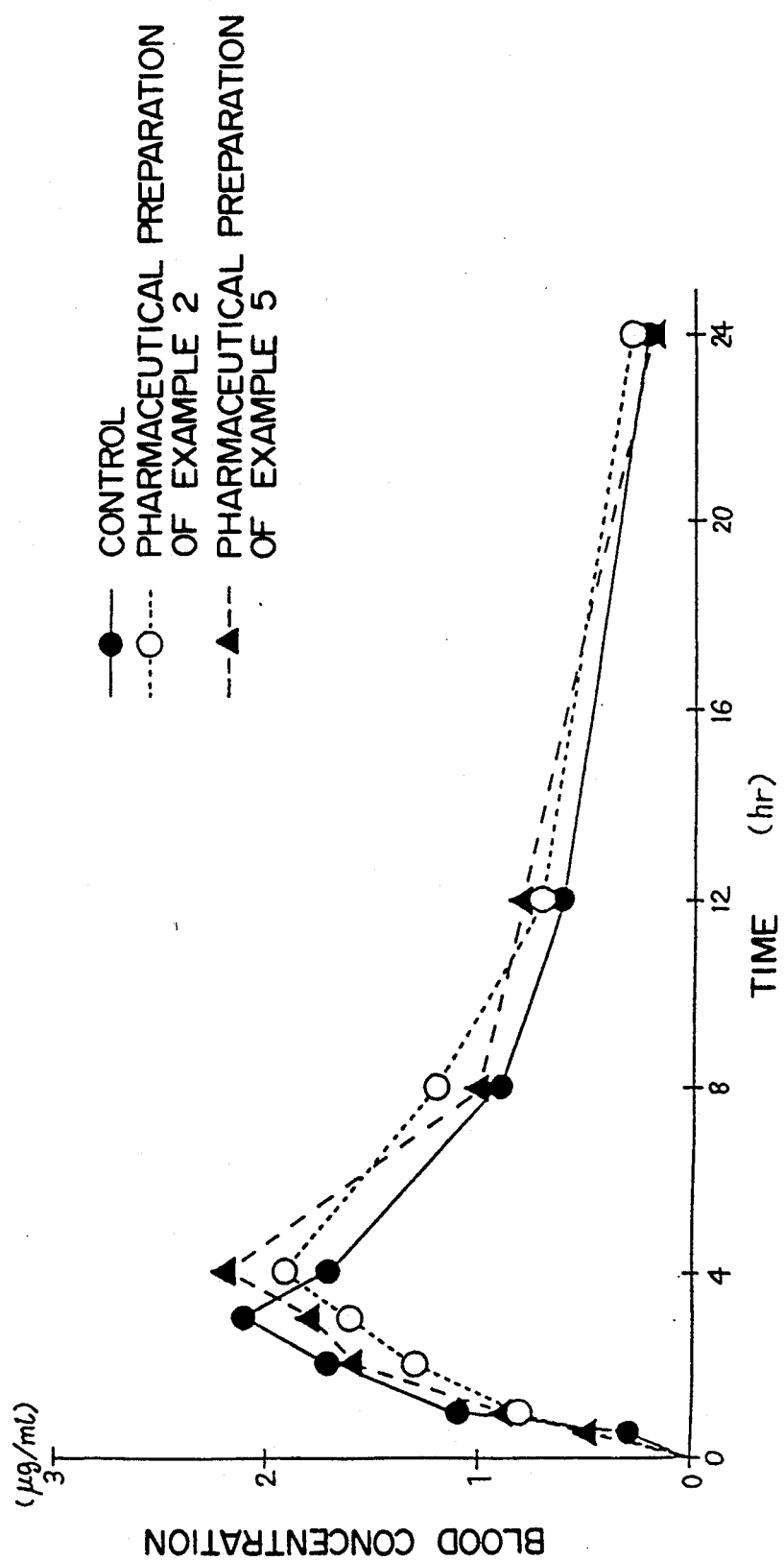

PROCESS FOR PRODUCING FLAVORED PHARMACEUTICAL PREPARATION FOR ORAL ADMINISTRATION USING A COLD WATER SOLUTION OF POLYVINYL ACETAL DIMETHYLAMINOACETATE

TECHNICAL FIELD

The present invention relates to a process for producing a flavored pharmaceutical preparation for oral administration and more particularly to a process for producing a flavored pharmaceutical preparation for oral administration wherein the taste of a drug contained therein is well masked.

BACKGROUND ART

Various flavored pharmaceutical preparations and their production processes have hitherto been known; however, no satisfactory flavored pharmaceutical preparation and production process thereof have been developed.

In view of such a situation, the present inventors provided an invention described in Japanese Patent Application Kokai (Laid-Open) No. 188621/1988. The invention provided a flavored pharmaceutical preparation for oral administration wherein the taste of a drug contained therein is well masked, as well as a process for producing said pharmaceutical preparation. In this production process, however, droplets varying in diameters are allowed to fall onto a powder bed to produce a flavored pharmaceutical preparation for oral administration; therefore, the process has had problems in that the separation of the powder bed and the pharmaceutical preparation is difficult and the yield of the pharmaceutical preparation is low.

It is an object of the present invention to solve the above problems caused by the use of the powder bed and to provide a process for producing a flavored pharmaceutical preparation for oral preparation wherein the taste of a drug contained therein is well masked.

DISCLOSURE OF THE INVENTION

The present invention relates to a process for producing a flavored pharmaceutical preparation for oral administration, characterized by spraying, in a moistened and heated air, a suspension of a drug or drug-containing particles dispersed in a cold water solution of polyvinyl acetal diethylaminoacetate (hereinafter referred to as AEA), and drying the resulting fine particles.

The production process of the present invention is described in detail below.

First, there is sprayed, in a moistened and heated air, a suspension of a drug or drug-containing particles dispersed in a cold water solution of AEA.

Herein, the drug refers to a solid drug which has an undesirable taste and is difficultly soluble in water, such as macrolide antibiotic (e.g. Erythromycin, 6-0-methylerythromycin A), anti-inflamatory analgesic (e.g. Ketoprofen, Ketophenylbutazone, Ibuprofen, Acetaminophen), antihistamine (e.g. Promethazine HCl), antitussive (e.g. Clobutinol HCl, Oxeladin Tannate), antidiarrheal agent (e.g. Berberine HCl), spasmolytic (e.g. Propantheline Bromide, Papaverine HCl), antithrombotic agent (e.g. naclopidine HCl), antirheumatic agent (e.g. Mefenamic acid, Flufenamic Acid), tranquilizer (e.g. Chloropromazine HCl, Promethazine HCl), cardiotoxic (e.g. Digitoxin, Aminophylline), gallstone-solubilizing agent (e.g. chenodeoxycholic acid), travail-inducing agent (e.g. Dinoprostone) or the like.

Further, drug-containing particles refers to fine particles obtained by dissolving a wall-forming substance (e.g. AEA, gelatin, emulsion polymer of methacrylic acid and ethyl acrylate, cacao butter) in a solvent (e.g. purified water, ethanol) under heating or at the ordinary temperature, suspending the above-mentioned drug in the resulting solution, introducing the resulting suspension into an atomizer by the use of a metering pump to effect spraying, followed by drying.

The "cold water" refers to a "cold water" of 10° C. or lower. AEA is dissolved therein at a concentration of 1-30% by weight. When the concentration of AEA is more than 30% by weight, AEA is insoluble in the cold water.

The moistened and heated air is an air of 20°-95° C., preferably 50°-90° C. having a relative humidity of 70% or more.

The spraying of the suspension is effected by introducing the suspension into an atomizer by the use of a metering pump while keeping the suspension at a temperature at which AEA causes no gelation. In this case, a jacket is fitted to the metering pump and the atomizer to keep their temperatures at the same level as that of suspension.

In the above procedure, it is important that the fine droplets formed (the suspension is sprayed and becomes fine droplets) be contacted with the moistened and heated air of the above conditions (the conditions necessary for gelation of AEA) to give rise to the gelation of AEA on the surface(s) of the drug or drug-containing particles to obtain fine particles.

Next, the fine particles obtained in the above procedure are dried.

In this case, the recovery of the fine droplets is easily effected by, for example, allowing the fine particles to fall into a water bath containing hot water and passing the resulting hot water (e.g. hot water of 20°-80° C.) through a sieve, or allowing the fine particles to fall onto a belt conveyor.

The drying is effected for 1 hour or more, preferably 8 hours or more (ordinarily about 12-24 hours) at 15°-80° C., preferably 20°-40° C. The drying is effected by a conventional dryer, for example, a fluidized bed dryer, a rotary type through flow dryer or the like.

By effecting the drying under the above conditions, the water contained in the AEA gel on the surface of the drug or drug-containing particles is removed gradually, whereby a dense film is formed and no porous film is obtained.

BRIEF DESCRIPTION OF DRAWING

FIG. 1 is a graph showing the bioavailabilities of the pharmaceutical preparations produced according to the production process of the present invention. In FIG. 1, the axis of ordinate refers to blood concentration and the axis of abscissa refers to elapsed time.

BEST MODE FOR CARRYING OUT THE INVENTION

The present invention is described in more detail below referring to Examples and Test Examples.

EXAMPLE 1

4 parts by weight of AEA were added to 95 parts by weight of purified water of 2° C. The resulting mixture was cooled to 0° C. with stirring, to completely dissolve AEA in the water. To the resulting solution was added 1 part by weight of Erythromycin, and the resulting mixture was stirred to uniformly disperse the drug in the solution, to prepare a suspension. The suspension was introduced into an atomizer by the use of a metering pump while being kept at a constant temperature and was sprayed in steam of about 50° C. to give rise to gelation. The resulting gel was allowed to fall into a water bath kept at 50° C. The resulting AEA-coated particles in the bath were passed through a sieve to take out. The particles were dried by a rotary type through flow dryer (PTA-30 manufactured by Ookawara Seisakusho) under conditions of 25° C. and 40% RH for 20 hours to obtain the intended pharmaceutical preparation.

The obtained pharmaceutical preparation showed a particle size distribution of 60–90 μm and had an Erythromycin content of 19.6%.

EXAMPLE 2

5 parts by weight of AEA was added to 90 parts by weight of ethanol and completely dissolved therein. To the resulting solution was added 5 parts by weight of 6-0-Methylerythromycin A (hereinafter abbreviated to TE-031), and the mixture was stirred to uniformly disperse the drug in the solution, to prepare a suspension. The suspension was subjected to spray drying in an atmosphere of 85°–150° C. to obtain drug-containing fine particles to later become a core substance.

Next, 4 parts by weight of the above fine particles were quickly and uniformly dispersed in 96 parts by weight of a 4 weight % aqueous AEA solution obtained by dissolving AEA in cooled water, and the resulting suspension was instantly introduced into an atomizer and sprayed in steam of about 50° C. to give rise to gelation. The resulting gel was allowed to fall into a water bath kept at 50° C. The resulting AEA-coated particles in the water bath were passed through a sieve to take out. The particles were dried by a rotary type through flow dryer under conditions of 40° C. and 30% RH for 10 hours to obtain an intended pharmaceutical preparation.

The obtained pharmaceutical preparation showed a particle size distribution of 60–90 μm and had a TE-031 content of 24.3%.

EXAMPLE 3

7.5 parts by weight of gelatin was added to 85 parts by weight of purified water. The resulting mixture was heated to 65° C. to dissolve gelatin. In the resulting solution was uniformly dispersed 7.5 parts by weight of Ibuprofen to prepare a suspension. The suspension, while being kept at a constant temperature, was introduced into an atomizer by the use of a metering pump and sprayed to obtain fine droplets. The fine droplets were cooled to 5°–10° C. to obtain fine particles.

Next, 4 parts by weight of the fine particles were uniformly dispersed in 96 parts by weight of a 4 weight % aqueous AEA solution obtained by dissolving AEA in cooled water, to prepare a suspension. The suspension, while being kept at a constant temperature, was introduced into an atomizer by the use of a metering pump, sprayed, and allowed to fall into a water bath kept at 50° C., to give rise to gelation. The resulting AEA-coated particles in the water bath were passed through a sieve to take out. The particles were dried by a rotary type through flow dryer under conditions of 20° C. and 40% RH for 36 hours to obtain an intended pharmaceutical preparation.

The obtained pharmaceutical preparation showed a particle size distribution of 60–80 μm and had an Ibuprofen content of 25.5%.

EXAMPLE 4

80 parts by weight of cacao butter having a saponification value of 188–195 and an iodine value of 35–43 was heated to about 60° C. to melt. To this liquid was added 20 parts by weight of Acetaminophen with stirring, to uniformly disperse Acetaminophen, to prepare a suspension. The suspension, while being kept at a constant temperature, was introduced into an atomizer by the use of a metering pump and sprayed to obtain fine droplets. Then, the fine droplets were cooled and solidified to obtain fine particles. Next, 4 parts by weight of the fine particles were uniformly dispersed in 96 parts by weight of a 4 weight % aqueous AEA solution obtained by dissolving AEA in cooled water, to prepare a suspension. The suspension, while being kept at a constant temperature, was introduced into an atomizer by the use of a metering pump, sprayed in steam of about 50° C. to give rise to gelation. The gel was allowed to fall into a water bath kept at 50° C. The resulting AEA-coated particles in the water bath were passed through a sieve for separation. The particles were dried by a rotary type through flow dryer under conditions of 18° C. and 50% RH for 48 hours to obtain an intended pharmaceutical preparation.

The obtained pharmaceutical preparation showed a particle size distribution of 60–90 μm and had an Acetaminophen content of 10.2%.

EXAMPLE 5

AEA-coated particles were obtained in the same manner as in Example 1 except that 1 part by weight of Erythromycin used in Example 1 was replaced by 1 part by weight of TE-031.

This pharmaceutical preparation had a TE-031 content of 18.8%.

TEST EXAMPLE 1

Bitterness-masking test

A bitterness test was carried out using the pharmaceutical preparations produced in Example 2 and Example 5. The test method was as follows. Each pharmaceutical preparation was weighed in 2.5 ml of a 30% aqueous sugar solution so that the amount of the drug in the pharmaceutical preparation became 200 mg, to prepare a suspension syrup. Each syrup was allowed to stand for about 30 minutes. The resulting syrup was held in the mouths of testers consisting of 10 male persons and 10 female persons for one minute and then discharged from their mouths. In five minutes after emptying the mouth, the degree of bitterness was evaluated according to the following five-level yardstick.

First level: No bitterness
Second level: Substantially no bitterness
Third level: Slight bitterness
Fourth level: Bitterness
Fifth level: Considerable bitterness The results are shown in Table 1.

TABLE 1

| Test sample | Five-level yardstick | Number of testers | |
|---|---|---|---|
| | | Male | Female |
| Pharmaceutical preparation of Example 2 | No bitterness | 7 | 6 |
| | Substantially no bitterness | 2 | 2 |
| | Slight bitterness | 1 | 2 |
| | Bitterness | 0 | 0 |
| | Considerable bitterness | 0 | 0 |
| Pharmaceutical preparation of Example 5 | No bitterness | 6 | 5 |
| | Substantially no bitterness | 2 | 2 |
| | Slight bitterness | 2 | 3 |
| | Bitterness | 0 | 0 |
| | Considerable bitterness | 0 | 0 |

TEST EXAMPLE 2

Bioavailability test

Using the same test samples as in Test Example 1, a bioavailability test for four male beagles was carried out. The test method was as follows. The beagles were fasted for 18 hours before the test. Then, a test sample was orally administered together with 50 ml of water so that the dose became 100 mg (in terms of TE-031) per one beagle.

After the administration, blood was collected from the foreleg of each beagle with the lapse of time to measure the blood concentraiton of drug by high performance liquid chromatography. As a control test, 100 mg of a powder of TE-031 itself was orally administered together with 50 ml of water, and its blood concentration was measured in the same manner.

The results are shown in FIG. 1.

As can be appreciated from FIG. 1, the powder of TE-031 itself and the TE-031 pharmaceutical preparations produced according to the process of the present invention show similar blood concentrations, indicating the high bioavailability of the pharmaceutical preparation produced according to the process of the present invention.

INDUSTRIAL APPLICABILITY

The present invention has made it possible to provide a process for producing a flavored pharmaceutical preparation for oral administraiton wherein the taste of a drug contained therein is well masked and whose bioavailability is as good as that of a powder of said drug itself, which process involves no difficulty in separating the pharmaceutical preparation produced from a powder bed, as seen in the process using a powder bed and which process has no reduction in yield of pharmaceutical preparation.

We claim:

1. A process for producing a flavored pharmaceutical preparation for oral administration, comprising spraying, into a moistened and heated air, a suspension of a drug or drug-containing particles dispersed in a cold water solution of polyvinyl acetal diethylaminoacetate, and drying the resulting fine particles, to obtain said pharmaceutical preparation with bitterness of the drug well-masked wherein said cold water solution is at a temperature of 10° C. or less prior to spraying.

2. A process for producing a flavored pharmaceutical preparation for oral administration according to claim 1, wherein the moistened and heated air has a temperature of 50°-90° C. and a relative humidity of 70% or more.

3. A process for producing a flavored pharmaceutical preparation for oral administration according to claim 1, wherein the drying time is 8 hours or more.

4. A process for producing a flavored pharmaceutical preparation for oral administration according to claim 1, wherein the drying temperature is 20°-40° C.

5. A process for producing a flavored pharmaceutical preparation for oral administration according to claim 3 wherein the drying time is 8 hours or more and the drying temperature is 20°-40° C.

6. A process for producing a flavored pharmaceutical preparation for oral administration according to claim 2 wherein the moistened and heated air has a temperature of 50°-90° C. and a relative humidity of 70% or more, the drying time is 8 hours or more and the drying temperature is 20°-40° C.

7. A process for producing a flavored pharmaceutical preparation for oral administration according to claim 4, wherein the drying time is 8 hours or more and the drying temperature is 20°-40° C.

8. A process for producing a flavored pharmaceutical preparation for oral administration according to claim 3, wherein the moistened and heated air has a temperature of 50°-90° C. and a relative humidity of 70% or more, the drying time is 8 hours or more and the drying temperature is 20°-40° C.

9. A process for producing a flavored pharmaceutical preparation for oral administration according to claim 4, wherein the moistened and heated air has a temperature of 50°-90° C. and a relative humidity of 70% or more, the drying time is 8 hours or more and the drying temperature is 20°-40° C.

10. The process of claim 1, wherein said spraying is by means of an atomizer and metering pump and wherein said atomizer and metering pump are cooled to maintain their temperature the same as that of said suspension.

11. The process of claim 1, wherein said cold water solution contains 1-30% by weight of said polyvinyl acetal diethylaminoacetate.

12. The process of claim 1 wherein said air contains steam.

13. The process of claim 1 wherein said air contains steam.

14. The process of claim 11 wherein said air contains steam.

* * * * *

UNITED STATES PATENT AND TRADEMARK OFFICE
CERTIFICATE OF CORRECTION

PATENT NO. : 5,227,171
DATED : July 13, 1993
INVENTOR(S) : KOYAMA et al

It is certified that error appears in the above-indentified patent and that said Letters Patent is hereby corrected as shown below:

Col. 2, line 3, "drug-containing agent" should read --"drug-containing agent"--.

Col. 3, line 29, "of" should read --at--.

Column 6, lines 53-54, delete claim 13.

Signed and Sealed this

Fourteenth Day of June, 1994

Attest:

BRUCE LEHMAN

*Attesting Officer*    *Commissioner of Patents and Trademarks*